United States Patent
Putz

(10) Patent No.: US 7,134,919 B2
(45) Date of Patent: Nov. 14, 2006

(54) MULTIPLE-USE, STIMULATION-ACCOMMODATING CONNECTOR

(75) Inventor: David A. Putz, Pewaukee, WI (US)

(73) Assignee: Ad-Tech Medical Instrument Corp., Racine, WI (US)

( * ) Notice: Subject to any disclaimer, the term of this patent is extended or adjusted under 35 U.S.C. 154(b) by 0 days.

(21) Appl. No.: 11/029,269

(22) Filed: Jan. 4, 2005

(65) Prior Publication Data

US 2006/0148326 A1    Jul. 6, 2006

(51) Int. Cl.
*H01R 13/10* (2006.01)

(52) U.S. Cl. .................................. 439/682; 439/909

(58) Field of Classification Search ............. 439/668, 439/909, 669, 682, 692; 600/378, 486, 393, 600/373, 377; 128/419 P; 607/115, 113, 607/37

See application file for complete search history.

(56) References Cited

U.S. PATENT DOCUMENTS

| | | | | |
|---|---|---|---|---|
| 4,712,557 A | * | 12/1987 | Harris | 607/37 |
| 4,850,359 A | | 7/1989 | Putz | 607/116 |
| 4,869,255 A | | 9/1989 | Putz | 439/72.9 |
| 4,898,173 A | * | 2/1990 | Daglow et al. | 607/37 |
| D340,913 S | * | 11/1993 | Miller | D13/154 |
| 5,743,754 A | * | 4/1998 | Cristich | 439/349 |
| 5,877,732 A | | 3/1999 | Ziarati | 345/8 |
| 6,162,101 A | | 12/2000 | Fischer et al. | 600/378 |
| 6,304,784 B1 | | 10/2001 | Allee et al. | 52/9 |
| 6,319,021 B1 | * | 11/2001 | Billman | 439/78 |
| 6,415,168 B1 | | 7/2002 | Putz | 600/378 |
| 6,649,838 B1 | * | 11/2003 | Lopez et al. | 174/67 |
| 6,662,035 B1 | * | 12/2003 | Sochor | 600/378 |
| 6,725,096 B1 | * | 4/2004 | Chinn et al. | 607/115 |
| 6,749,604 B1 | | 6/2004 | Eggers et al. | 606/41 |

OTHER PUBLICATIONS

Roby, Robert J. and Lettich, Ettore; "A Simplified Circuit for Stimulus Artifact Suppression," Electroencephalography and Clinical Neurophysiology, 1975, 39: pp. 85-87.

Liem M.D., Leon K., "Intraoperative Neurophysiological Monitoring," 13 pages. 2004. <www.emedicine.com>.

Meyer, B-U, Irlbacher, K., and Meierkord, H. "Analysis of stimuli triggering attacks of paroxysmal dystonia induced by exertion," J Neurol Neurosurg Psychiatry 2001; 70: 247-251 (Feb.); <http://jnnp.bmjjournals.com/cgi/content/full/70/2/247>.

(Continued)

*Primary Examiner*—Alexander Gilman
(74) *Attorney, Agent, or Firm*—Jansson, Shupe, Munger & Antaramian, Ltd.

(57) ABSTRACT

A multiple-use connection system includes an elongate body having an axial tail-receiving passage and having lengthwise sides, and at least two essentially parallel rows of axially-spaced pin receptacles transverse to the tail-receiving passage, the pin receptacles of one of the parallel rows being exposed along one of the lengthwise sides. A patchbay for selectively connecting pairs of connector pins with ones of a plurality of tail conductors includes an insulating body having an axial passageway adapted for receiving a tail and having pairs of aligned pin receptacles, the pairs of pin receptacles being axially spaced from one another, one pin receptacle of each of the pairs of pin receptacles having an exposed portion adapted for being directly probed, where selective placement of pairs of aligned pins into the insulating body effects electrical connection of a pair of pins to a selected one of the tail conductors.

32 Claims, 13 Drawing Sheets

OTHER PUBLICATIONS

T Kujirai, et al. "Corticocortical inhibition in human motor cortex," The Journal of Physiology, vol. 471, Issue 1 501, Physiological Society (1993).

"BMSI Cortical Stimulator Switch Box," product literature, Feb. 24, 1995. Nicolet BMSI, A Division of Nicolet Biomedical Inc.

Harding, G.W., and Towe, A.L., "Wide-field neurons and direct cortical stimulation," Washington University Medical School.

National Institute of Neurological Disorders and Stroke (NINDS), "Multichannel Transcutaneous Cortical Stimulation System," <http://accessible.ninds.nih.gov/npp/sow/stm256.htm>.

* cited by examiner

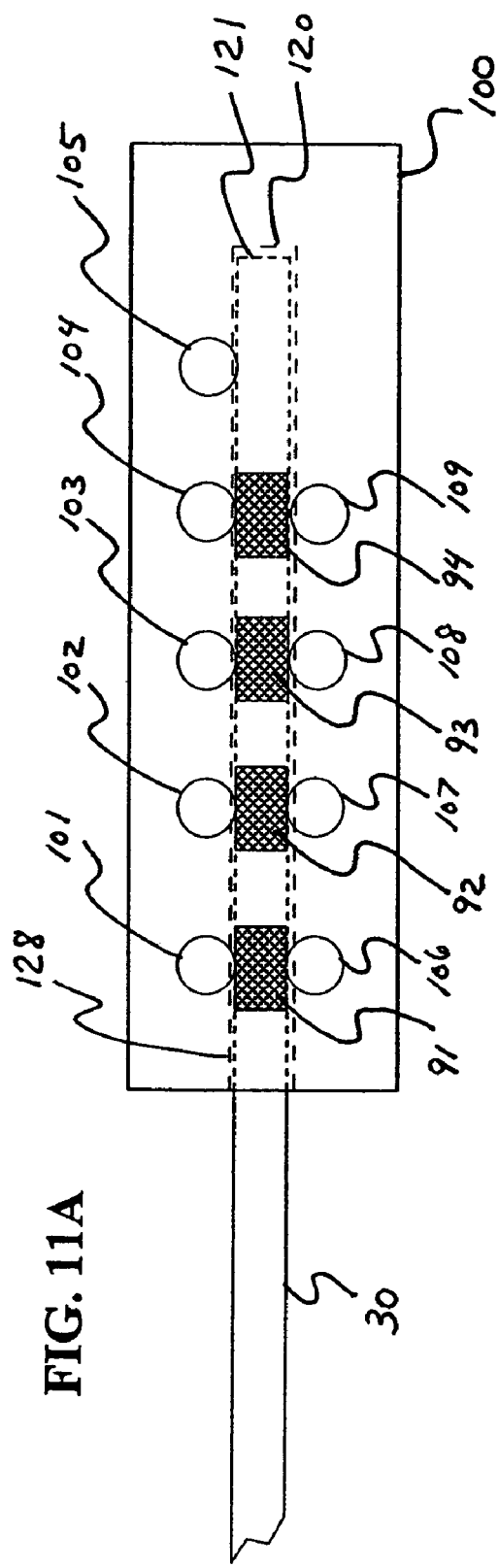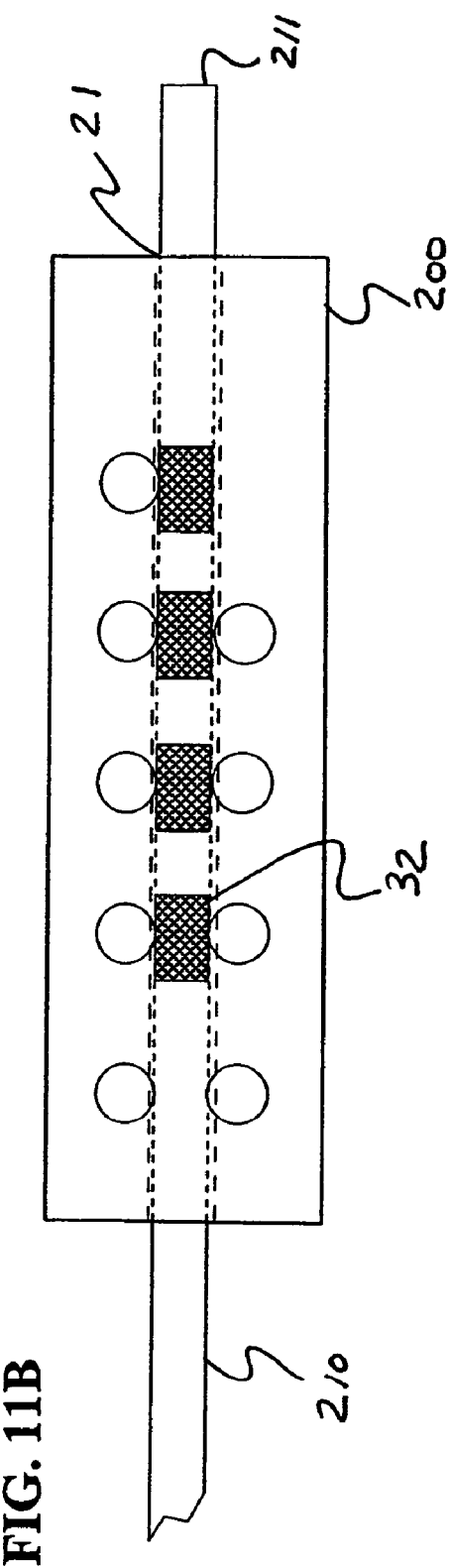
FIG. 11A
FIG. 11B

MULTIPLE-USE, STIMULATION-ACCOMMODATING CONNECTOR

FIELD OF THE INVENTION

The invention relates generally to devices for providing electrical connection between conductors and, more particularly, to connectors facilitating probing or stimulating chosen conductors being connected.

BACKGROUND OF THE INVENTION

Accurate sensing of intracranial electrical activity, such as for determining epileptogenic foci or otherwise, may require use of a plurality of brain contacts. Epileptogenic mapping is one example of the use of electrical devices with tissue-engagement contacts. Examples of two kinds of intracranial electrical contact devices are depth probes and flexible flat surface members.

Depth probes, which may be referred to as "depth electrodes," penetrate deep into the brain tissue. On the other hand, flexible flat surface members, including what are sometimes referred to as "strip" electrodes and "grid" electrodes, may be placed subdurally in direct contact with brain tissue at the surface of the brain.

Each of these different kinds of intracranial tissue-engagement members may have a plurality of electrodes which are separated from one another by a non-conductive material on which the electrodes are mounted. Separate thin insulated lead wires extend from the tissue-engagement member for each electrode. Such lead wires extend away from the tissue-engagement member to one or more connectors connecting the lead wires with individual conductors, for example, for distributing individual electrode circuits to monitoring or recording equipment.

Conventional connection systems such as those used with apparatus for monitoring brain tissue are not adapted for selective direct connection of probes and the like to individual conductors, such as for applying stimulation signals. Such conventional systems constrain a user, such as when it is desired to monitor or stimulate very small signals. Similarly, impedance mismatches can occur when a probe or the like is not properly placed. In addition, noise may be allowed to intrude as a result of inefficiencies and poor electrical design of such conventional systems, and logistical problems may be created, such as by use of adapters, extra wiring, etc. In another example, conventional systems may require disconnection of one piece of equipment (e.g., EEG) before being able to apply a stimulus to particular conductor (s), or may restrict a corresponding stimulation signal magnitude. Further, conventional systems are not adapted for use with magnetic resonance imaging (MRI) concurrently with epileptogenic monitoring. Disconnection of a first connector and connection of a second connector takes time, and creates the opportunity for error and equipment breakage. Additional problems with conventional systems may occur due to extra setup time, extra procedures and their resultant cost, setup complexity and resultant possibility for error such as incorrect hookup, additional problems of open circuits and short circuits, etc.

OBJECTS OF THE INVENTION

It is an object of the invention to provide an improved electrical connector for brain-contact devices overcoming certain problems of the prior art, including those mentioned above.

Another object of the invention is to provide an improved electrical connection system which facilitates various surgical procedures, such as those related to cortical stimulation, without a need for disconnecting external monitoring equipment.

Another object of the invention is to provide a connection system that facilitates monitoring of weak signals as well as stimulation using large signals.

Another object of the invention is to provide a system adaptable for multi-dimensional connection between circuits, such as by providing matrix-type connectivity between different coordinate axes.

Another object of the invention is to provide a connection system for electrical brain-contact devices which may be electrically connected easily and quickly during surgical placement and set-up procedures.

Another object of the invention is to provide an electrical connector which resists breakage of lead wires during insertion of brain-contact devices.

Another object of the invention is to provide an electrical connector which provides rapid and accurate electrical hookup of large numbers of electrodes and lead wires during surgical procedures.

Another object of the invention is to provide an electrical connector for plural lead wires which is simple in construction and operation.

These and other important objects will be apparent from the descriptions that follow.

SUMMARY OF THE INVENTION

According to an aspect of the invention, a multiple-use connection system includes an elongate body having a first axial tail-receiving passage and having lengthwise sides, and at least two essentially parallel rows of axially-spaced pin receptacles, the pin receptacles being transverse to the tail-receiving passage, the pin receptacles of one of the parallel rows being exposed along one of the lengthwise sides of the elongate body.

According to another aspect of the invention, a patchbay for selectively connecting pairs of connector pins with ones of a plurality of tail conductors includes an insulating body having an axial passageway adapted for receiving a tail with the plurality of tail conductors, and having pairs of aligned pin receptacles, the pairs of pin receptacles being axially spaced from one another, one pin receptacle of each of the pairs of pin receptacles having an exposed portion adapted for being directly probed, where selective placement of pairs of aligned pins into the insulating body effects electrical connection of a pair of pins to a selected one of the tail conductors.

According to another aspect of the invention, a method includes implanting an electrode array for electrical monitoring of a corresponding plurality of locations of a brain, the electrode array having at its distal end a multiconductor, annular ring type tail, inserting the tail into a multiple-use connector body, and connecting pins of a multiconductor cable assembly to respective conductors of the tail, thereby immobilizing the tail within the multiple-use connector body, whereby at least two of the connected pins are exposed along a side of the multiple-use connector body.

According to another aspect of the invention, a method for selectively implementing monitoring and stimulation of an electrode array includes providing an implantable electrode array having a plural-contact tail, providing a cable having a plurality of conductors terminating at a corresponding plurality of pins, and providing a connector body having an axial tail-receiving passage and lengthwise sides, the connector body being adapted for engaging the pins, thereby electrically connecting contacts of the plural-contact tail with respective conductors of the multiconductor cable via the engaged pins, where the connector body is adapted for selectively probing ones of the plurality of pins without disengaging the pins from the connector body.

According to another aspect of the invention, a method of implementing a patchbay includes providing an elongate body having an axial tail-receiving passage and having lengthwise sides, providing at least two essentially parallel rows of axially-spaced pin receptacles, aligned pairs of the pin receptacles being transverse to the tail-receiving passage, the pin receptacles of one of the parallel rows being exposed along one of the lengthwise sides of the elongate body, and providing a system for implementing selectable interconnectivity between individual ones of the pin receptacles.

According to another aspect of the invention, a method includes providing a connector having an elongate body having a first axial tail-receiving passage and having lengthwise sides, the connector also having at least two essentially parallel rows of axially-spaced pin receptacles, the pin receptacles being transverse to the tail-receiving passage, the pin receptacles of one of the parallel rows being exposed along one of the lengthwise sides of the elongate body, and providing a plug having at least two rows of essentially parallel pins and being structured for being inserted into the connector in at least two different ways.

As a result of various implementations of the invention, an improved electrical connector for brain-contact devices overcomes certain problems of the prior art.

The foregoing summary does not limit the invention, which is instead defined by the attached claims.

BRIEF DESCRIPTION OF THE DRAWING FIGURES

FIG. 11A is a top view of a connector showing electrical connection locations between pin receptacles of the connector and electrical contact locations of a multi-conductor tail inserted a predetermined distance into the connector, according to an exemplary embodiment of the invention; FIG. 11B is a top view of a feed-through type connector showing electrical connection locations between pin receptacles of the connector and electrical contact locations of a multi-conductor tail inserted into and through a connector, according to an exemplary embodiment of the invention.

Figure 1:
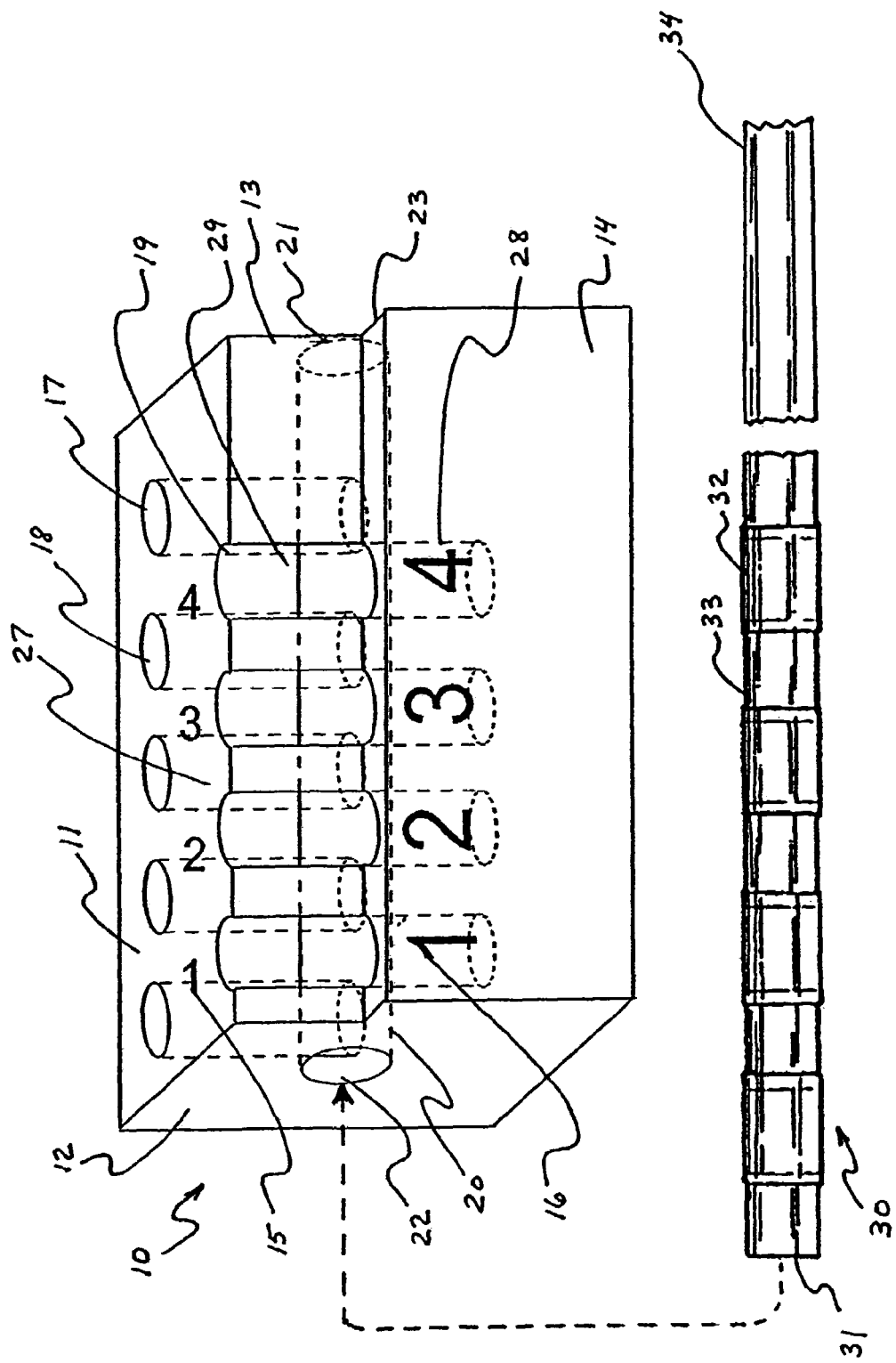
FIG. 1 is an enlarged perspective view of a connector and a front elevational view of a multi-conductor tail for insertion into the connector, according to an exemplary embodiment of the invention.
Figure 12:
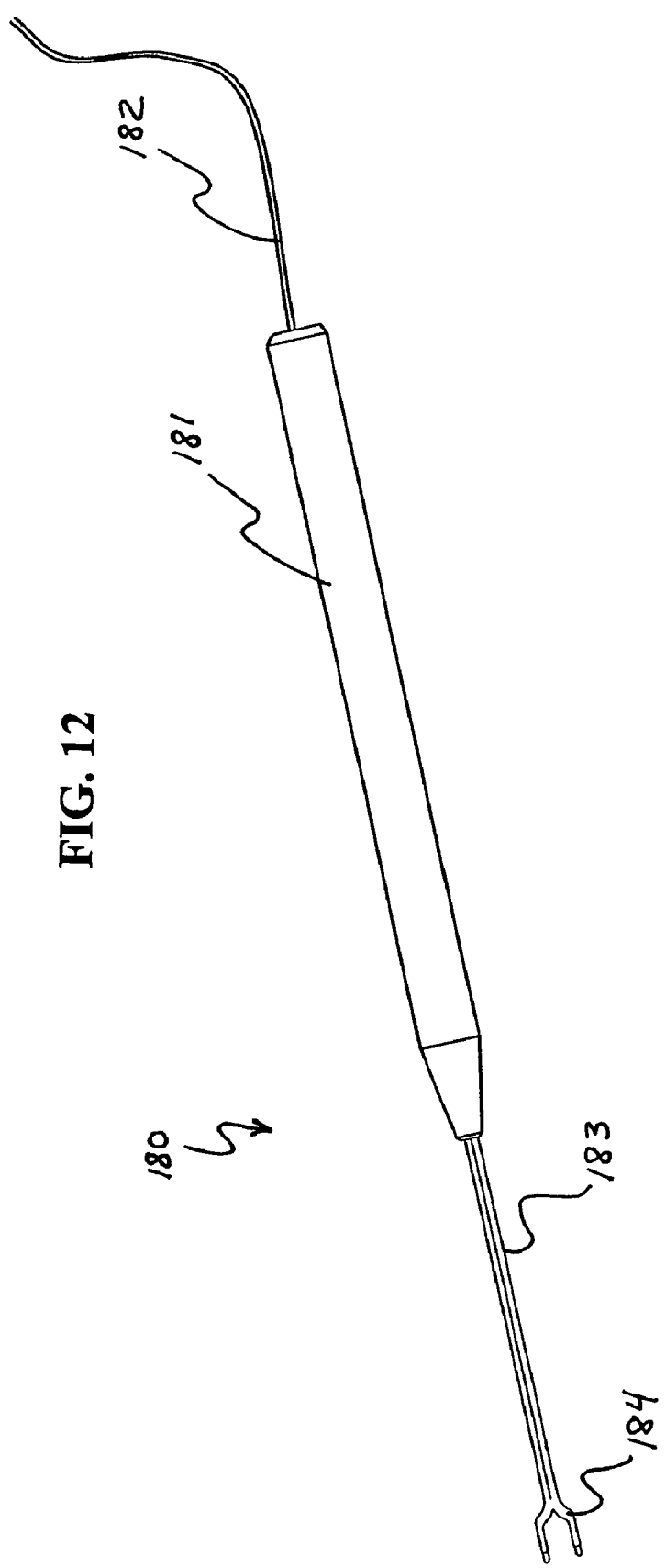

FIG. 12 shows an exemplary bipolar stimulator device that may be used for providing an external input to the connector of FIG. 1.

Figure 13:
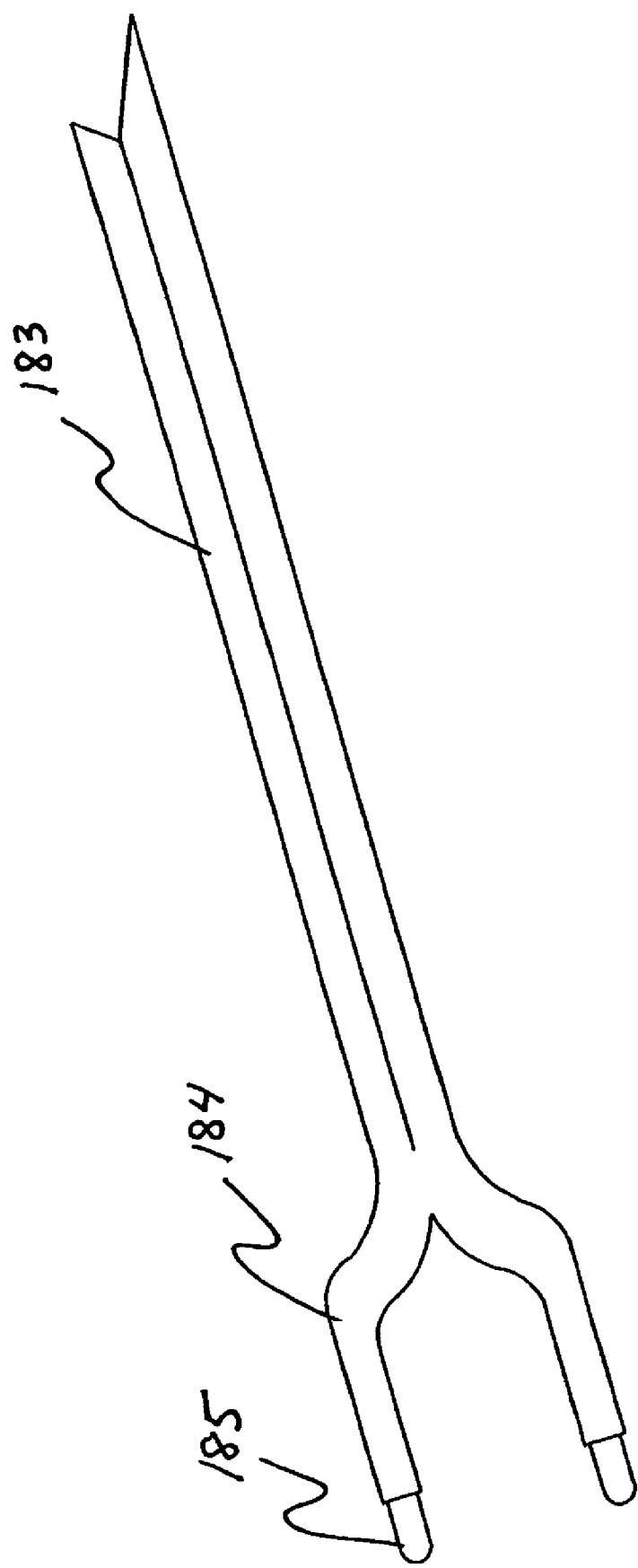

FIG. 13 shows an enlarged view of the probe portion of the bipolar stimulator device of FIG. 12.

Figure 14:
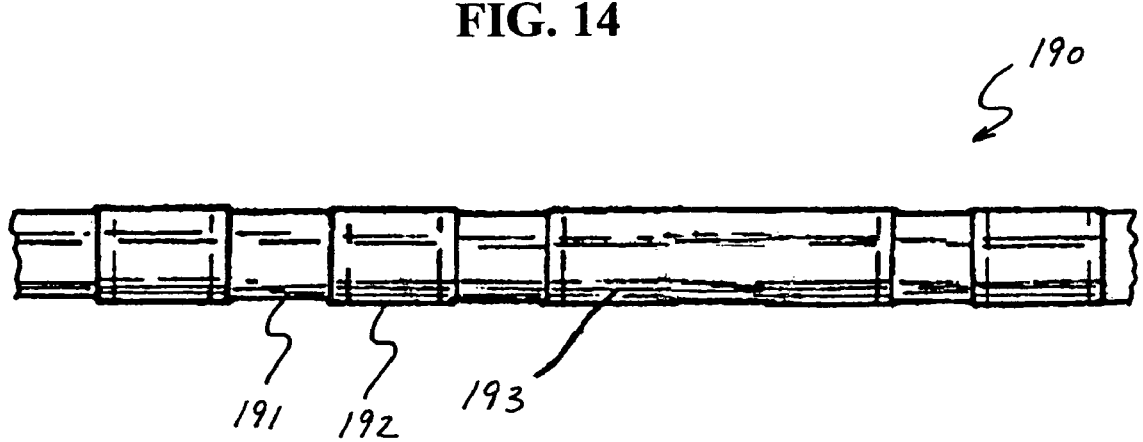

FIG. 14 is a side elevational view of a portion of a multi-conductor tail adapted for providing a patchbay type interconnectivity when used in a connector system according to an exemplary embodiment of the invention.

Figure 15:
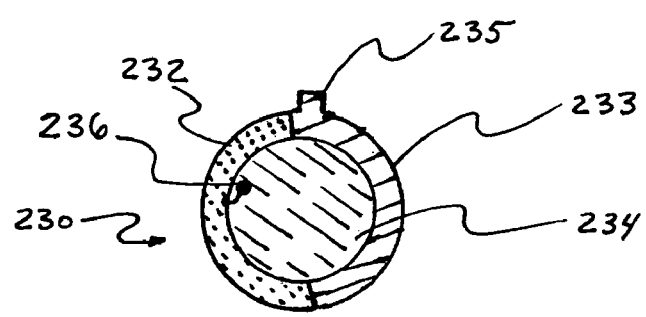

FIG. 15 is a cross-sectional view of a multi-conductor tail according to an exemplary embodiment of the invention.

Figure 16:
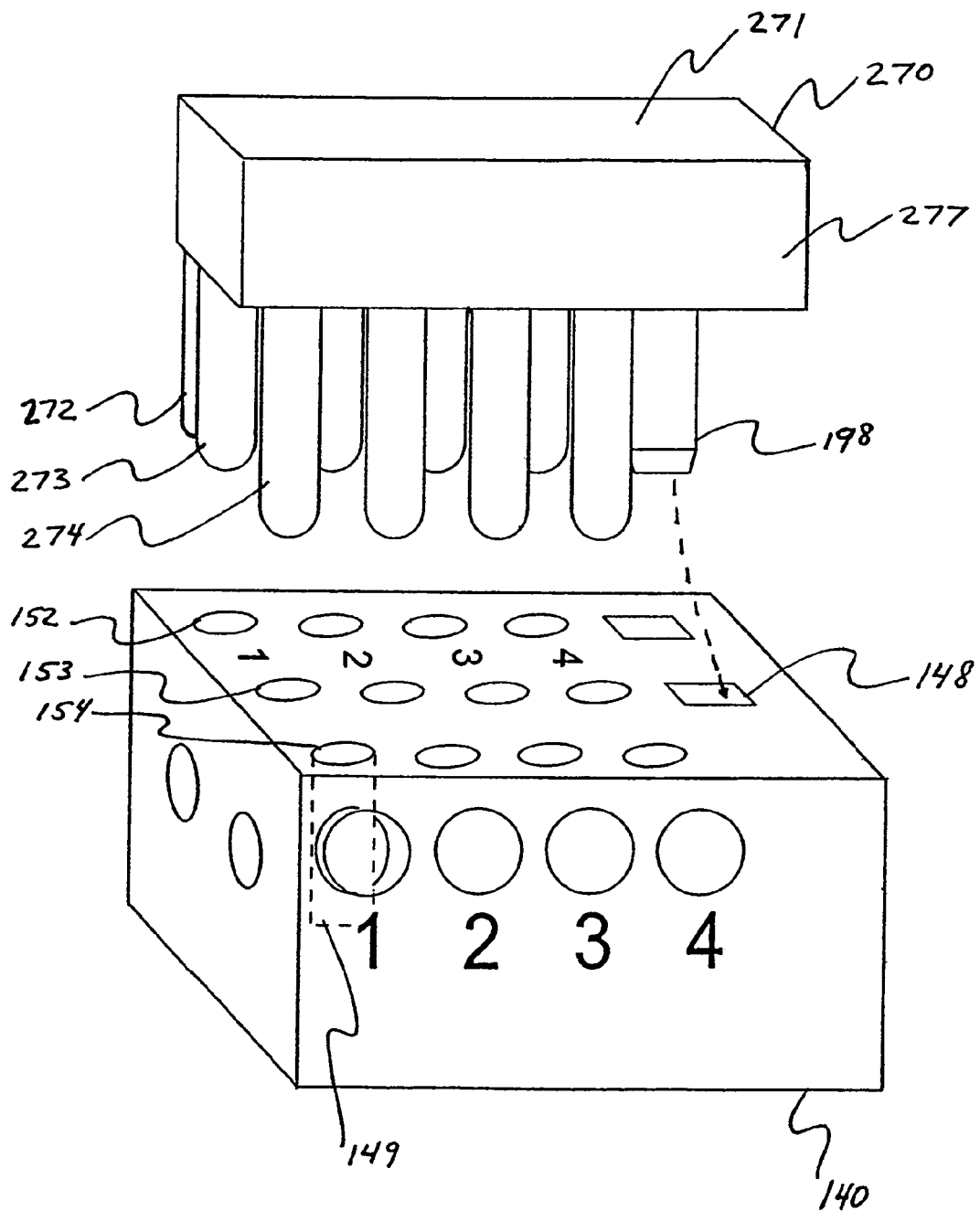

FIG. 16 is an enlarged perspective view of a connection system that includes a three-row connector having side access ports and a port cover strip, and that includes a connector having a corresponding three rows of pins, according to an exemplary embodiment of the invention.

Figure 17:
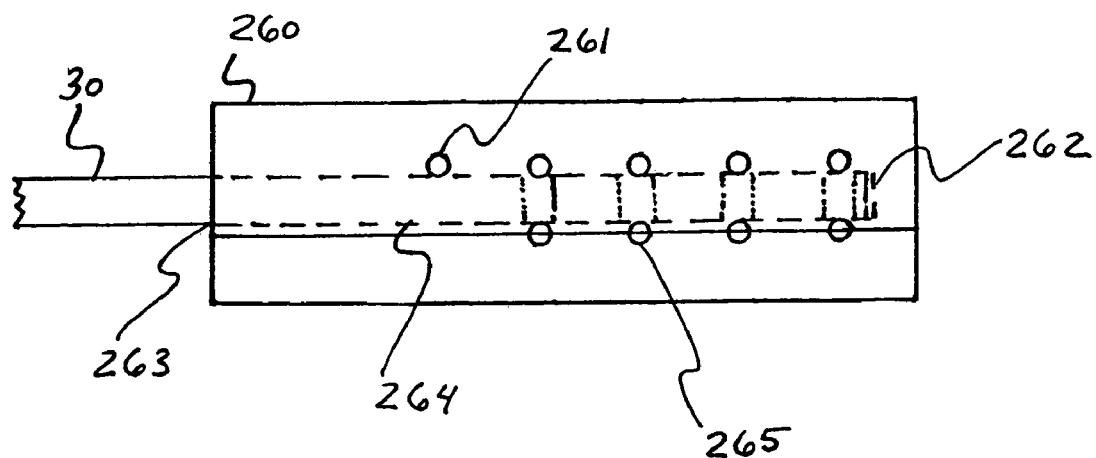

FIG. 17 is a top view of a connector showing electrical connection locations between pin receptacles of the connector and electrical contact locations of a multi-conductor tail inserted into the connector, according to an exemplary embodiment of the invention.

DETAILED DESCRIPTION OF PREFERRED EMBODIMENTS

Figure 2:
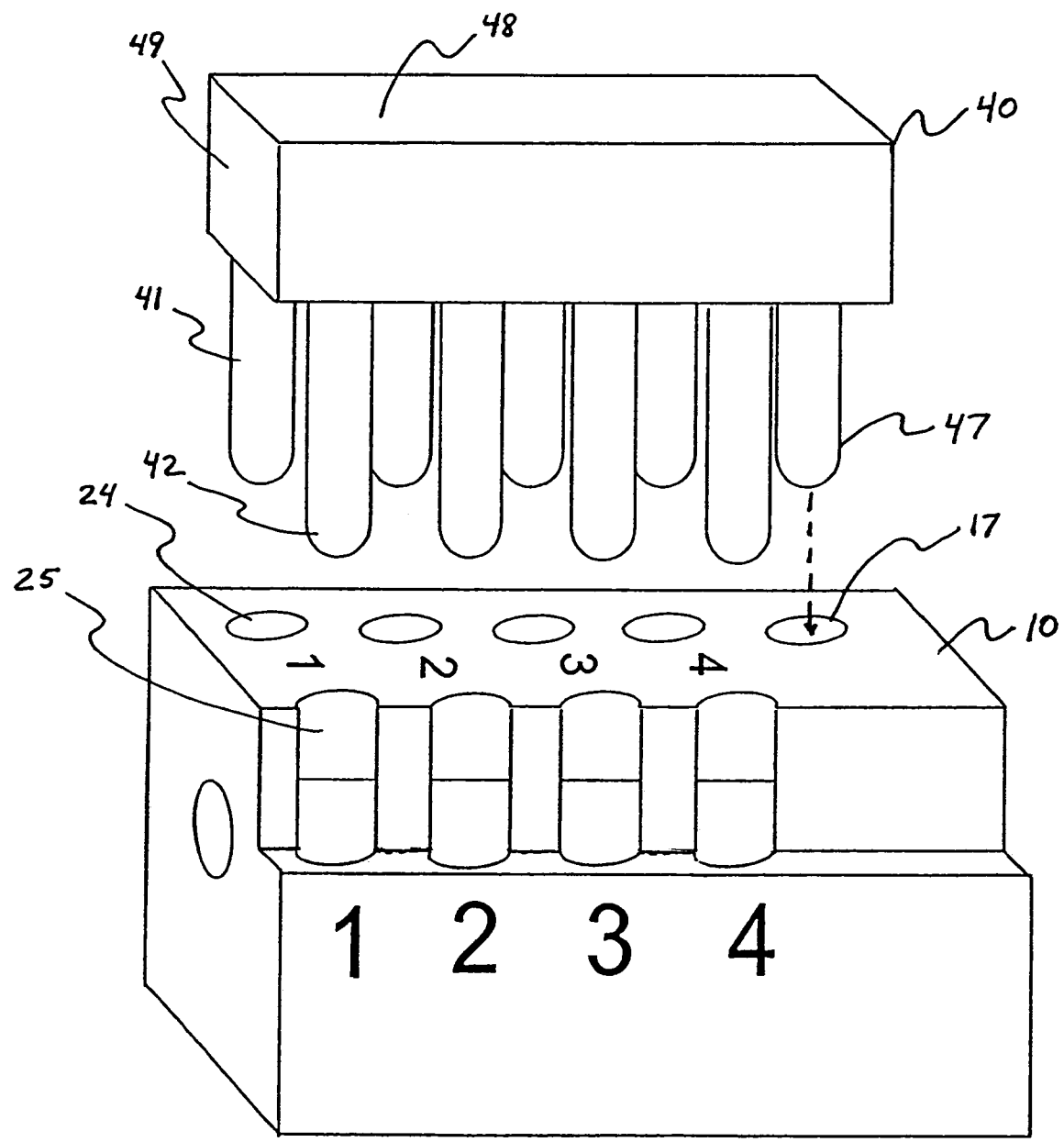
FIG. 2 is an enlarged perspective view of the connector of FIG. 1 together with a plug adapted for insertion into the connector, according to an exemplary embodiment of the invention.

FIG. 1 shows a connector 10 and a multi-conductor tail 30 for insertion into connector 10, according to an exemplary embodiment of the invention. FIG. 2 shows connector 10 together with a plug 40 adapted for insertion into the connector. FIGS. 3–6 show exemplary embodiments of subdural strip and grid type electrodes used in surgical procedures and having multi-conductor tails with a form similar to that of tail 30. Although not shown, the various embodiments of the invention may also each be used with various other electrodes such as depth electrodes and the like.

Connector 10 may be formed using a variety of readily available parts and materials, and is preferably formed by a molding or machining process using a polysulfone or polycarbonate resin. A suitable material is the polycarbonate resin known as LEXAN, available from General Electric, Schenectady, N.Y. Preferably, connector 10 is formed with such material being substantially transparent. Use of a substantially transparent material allows observation of the engagement of male connector pins of plug 40 with terminal rings 32 of tail 30. An example of such a connection is shown in FIG. 11, described further below. Terminal rings 32 of tail 30 are separated by insulating portions 33 and are preferably sequentially spaced a consistent distance from adjacent terminal rings 32, such spacing preferably being the same as a spacing between each adjacent pair 41, 42 of pins of plug 40.

Connector 10 is preferably of unitary construction, being entirely free of conductive material, and in a preferred embodiment is intended to be discarded after use. In other embodiments, a connector may be formed to include electrical interconnections formed with metal inserts, such as for connecting selected circuits together as is discussed further below. In addition, connector 10 may be a single block with any number of receptacles 17, 18, 19 or, for example, connector 10 may be formed of a plurality of sub-blocks which are attached end-to-end by mating attachment of each adjacent pair of sub-blocks.

A top surface 11 of connector 10 has two rows of vertically-oriented receptacles, shown by way of example in FIG. 1 as completely-enclosing type receptacles 18 in a first row and partially-exposed type receptacles 19 in a second row. As shown, the first row of vertically-oriented receptacles also includes a keying type receptacle 17. Such a keying type receptacle may be formed in many different configurations and is generally intended to insure that pins being plugged into receptacles 18, 19 are correctly oriented and inserted in a desired receptacle. A keying receptacle and corresponding keying pin of any of the various embodiments may be of any chosen shape, and may optionally be used as an additional electrical pathway that provides an extra conductive connection.

Receptacle type 19 is formed to have an upper semi-circular portion 29 created by an inner vertical wall 13 extending from upper surface 11 to a depth-wise lateral surface 23, and is formed to have a lower, completely-enclosed portion 28 below lateral surface 23. Receptacle types 17, 18 each have vertical shafts 27 that are fully enclosed for their entire length. A series of top surface numbers 15 are formed in top surface 11 between laterally opposed pairs of receptacles 18, 19, the receptacles of each of the pairs being aligned laterally with one another. A corresponding series of side surface numbers 16 are aligned with receptacle types 19 along side surface 14. As is discussed further below, such side surface numbers may be used for placement of probe contacts on a particular set of numbered side access ports and as an indication of corresponding electrode contact to particular termination points of the connector.

Each receptacle type 17, 18, 19 extends vertically as a cylinder into the body of connector 10, for each receptacle of the two rows of receptacles. The receptacles 18, 19 of the two rows are aligned laterally with one another. For example, as shown in FIG. 1, an entry end 22 of a lengthwise passageway 20 of connector 10 receives end 31 of tail 30. When fully inserted, end 31 reaches distal tail-receiving end 21 of lengthwise passageway 20 of connector 10, which may be formed either as a closed end or as an open end for passing tail 30 therethrough. Tail 30 may have any number of conductive bands 32, and may be of any chosen length. For example, a tail length may depend on lengthwise alignment of conductive bands 32 with respective centers of adjacent receptacle holes 17, 18, which may necessitate that the length be such that end 31 of tail 30 be a predetermined distance from an adjacent one of conductive bands 32. A single-ended tail-receiving passageway is sometimes referred to as a "blind hole" type passageway, and may have a fixed length so that when a tail is inserted therein, the end of such tail abuts an endstop of the passageway, which aligns the conductive bands 32 in a desired location. When passageway 20 is a pass-through type, the distance between tail end 31 and the adjacent conductive band 31 is not limiting of the just-described lengthwise alignment. As discussed further below, an electrode assembly and its tail may have any number of conductive bands for such a pass-through connector.

In another example shown in FIG. 11A, tail 30 is first inserted into connector 100 and then pushed all the way in so that conductor bands 91, 92, 93, 94 are respectively aligned between corresponding receptacle pairs. When an inserting end 121 of tail 30 has been pushed all the way into connector 100, end 121 abuts an endstop 120 of passageway 128, thereby providing the desired alignment. Then, a plug (not shown) is inserted so that its pins 101–109 are inserted into the receptacles. Pins 101–109 are preferably of a type having a cylindrical form with tapered ends and coated with a highly conductive material such as gold, silver, and the like. As shown, pins 101 and 106 each abut an opposite side of conductor band 91, pins 102 and 107 each abut an opposite side of conductor band 92, pins 103 and 107 each abut an opposite side of conductor band 93, pins 104 and 108 each abut an opposite side of conductor band 94, and keying pin 105 is adjacent a side of tail 30.

In this connected state, tail 30 preferably is prevented from being pulled out because the snug engagement of each pair of inserted pins with each corresponding conductor band acts to slightly compress the conductor band and prevent movement of tail 30. In other words, plug 40 pins and individual conductors of tail 30 are held in firm engagement by mechanical interference. For example, individual pins of each numbered pair of plug pins may be spaced from each other by a distance less than the fixed cross-dimension of the corresponding tail conductor. This dimensioning requires forcible spreading of the pins of each pair for engagement with the corresponding conductor band. The forcible spreading provides the biasing means for reliable electrical contact and mechanical engagement.

When plug 40 is removed, tail 30 is then able to be removed, installed, or aligned in a desired configuration. When connector 100 is formed of a clear material, a user can visually check to make sure conductor bands 91–94 are properly aligned with pins 101–104 and 106–109, which provides assurance of proper connection. As is discussed further below, tail 30 may be inserted so that its conductive bands 91–94 are aligned in selected locations. As a result, placement of tail 30 in any of several locations can effect a "patchbay" type structure where, for example, an external circuit corresponding to a numbered pin location 15 can be selectively connected to a particular conductor of tail 30. Numbers (not shown) or colors may be formed on tail 30 adjacent the individual conductors for identifying, documenting, and effecting a desired "patch" of circuits. However, when a selectable patch is not a desired option, a nominal configuration may simply be designed for fully inserting tail 30 and where for respective inner and outer pins 41, 42 to be inserted into corresponding receptacles 24, 25 of a first position numbered "1," a keying pin 47 to be inserted into keying receptacle 17, and a distal end 21 to be closed so that tail 30 has its conductive rings 32 aligned properly when tail 30 is fully inserted.

In another example shown in FIG. 11B, a connector 200 is a pass-through type, so that tail 210 may be fed, for a given patch, to align a chosen conductor ring 32 with a selected pin location. In the illustrated example, by passing tail end 211 a chosen distance past distal connector end 21, an unlimited linear travel of tail 210 is allowed with respect to connector 200. In a different patch, a desired alignment may require tail end 211 to be positioned within the body of connector 200. In this manner, an indefinite number of conductors 32 and/or a variety of tail lengths may be used. For example, in the event that an electrode array for a particular surgical procedure is out-of-stock and an array having a larger number of electrodes and a corresponding larger number of conductive bands is being used as a replacement, the pass-through connector 200 allows a user to align the chosen conductor bands 32 in a desired location to obtain the desired patch, without being concerned with a connector having an endstop.

A variety of conductive materials may be used for lead-wire terminal rings 32, as would be well known to those skilled in the art. Lead-wires (not shown) are preferably stainless steel, platinum, or silver strands which are insulated by a teflon coating layer. The relative safety of subdural strip electrodes lies in the fact that, unlike depth electrodes, they are not invasive of brain tissue. By comparison, depth electrodes are narrow, typically cylindrical dielectric structures with contact bands spaced along their lengths. Depth electrodes are inserted into the brain in order to establish good electrical contact with different portions of the brain. Subdural strip electrodes, on the other hand, are flat strips supporting contacts spaced along their lengths. Such strip electrodes are inserted between the dura and the brain, along the surface of and in contact with the brain, but not within the brain.

Figure 3:
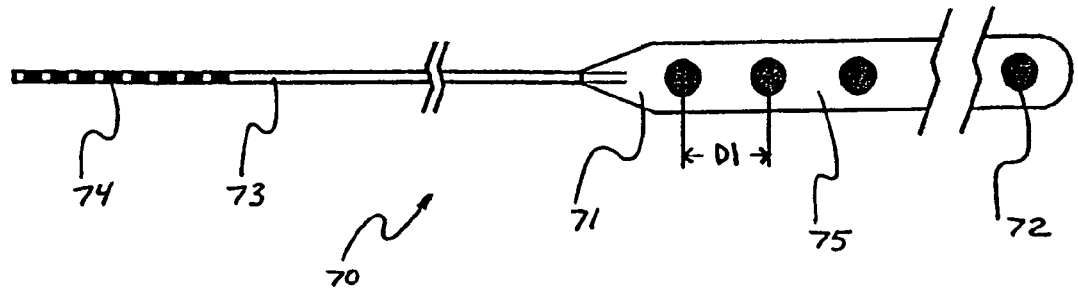
FIG. 3 shows an electrode strip that is of a type having a multi-conductor tail adapted for insertion into the connector of FIG. 1.
Figure 4:
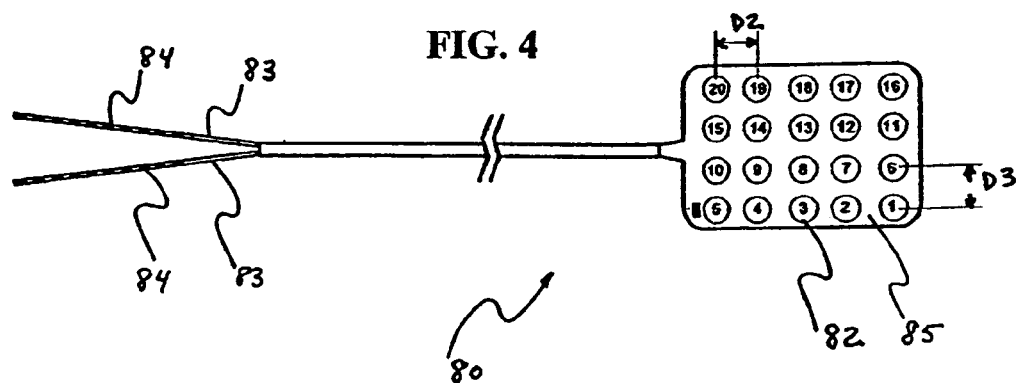
FIG. 4 shows an electrode grid that is of a type having a multi-conductor tail adapted for insertion into the connector of FIG. 1.
Figure 5:
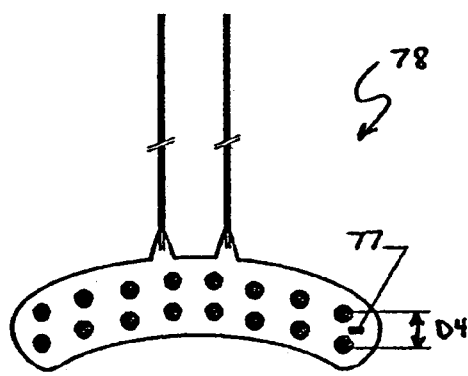
FIGS. 5 and 6 show different configurations for electrode arrays, such as dual-sided interhemispheric electrode arrays that is of a type having a multi-conductor tail adapted for insertion into the connector of FIG. 1.
Figure 6:
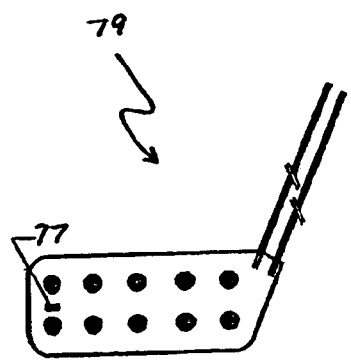

FIG. 3 shows a subdural electrode strip 70 and FIGS. 4–6 show examples of subdural grid electrodes. For example, subdural electrode strip 70 may be as disclosed in U.S. Pat. No. 6,004,262, granted to Putz et al. and herein incorporated by reference. The dielectric material used in such subdural electrodes is a flexible, medically-acceptable material such as silicone. Flexible sheet material 75, 85 is preferably a dielectric silicone sheet material such as medical grade silicone. Related structure such as tubular sheathing may also be formed of medical grade silicone or of a medical grade polyurethane. A variety of other suitable non-conductive materials may be used in forming an electrode array and tail(s). Subdural strip electrode assembly 70 has an elongated flexible dielectric strip 71 within which a plurality of spaced aligned flat contacts 72 and their lead wires are enclosed and supported in place, sandwiched between front and back layers of material forming the dielectric strip 71. Each flat contact 72 has a face or main contact surface which is exposed by an opening in the front layer of the dielectric strip. Contacts may be formed of material such as gold or platinum though, as is recognized in the art, any conductive corrosion-resistant and non-toxic material may be used.

Electrode strip 70 has a tail portion formed of a small-diameter, elongate, cylindrical, flaccid, flexible, electrically insulating material such as a silicone material or a polyurethane as the tail body 73. The body 73 has collar-like, tubular electric contacts 74 closely fitted around its outside surface. Each contact 74 is permanently attached to a separate insulated wire (not shown) that extends from the contact 74 through the body 73 to the respective electrode 72. The electrodes 72 may be formed of platinum, stainless steel, or other appropriate conductive material. Spacing between adjacent electrodes 72 (i.e., center-contact to center-contact) may be chosen in general in a range from about 2 to 15 mm. For example, a standard 10 mm spacing D1 between adjacent electrodes 72 may be adequate or, alternatively, a particular spacing between adjacent electrodes 72 may be customized for a particular application such as for different size cortex or for different resectioning operations, etc. Similarly, a diameter of individual electrodes 72 may be chosen in a range from about 0.5 to 10 mm. A 4–6 mm size with a corresponding 2–4 mm of exposure is typical. Subdural electrode strip 70 is characterized in that it provides advantages by being transparent, thin, flexible, and available in a variety of different sizes. Tails 73 of electrode strips 70 are typically either 1.5 mm or 2 mm in diameter. The latter may be used in standard DIN type connectors.

FIG. 4 shows a subdural electrode grid 80 formed as an array of electrodes 82. In this example, a four by five grid is chosen, but the arrangement and number of electrodes 82 in a grid 80 may be chosen for a particular application. For example, various subdural electrode grids are available from Ad-Tech Medical Instrument Corporation of Racine, Wis. A number of tails 83 depends on the electrode configuration. Here, subdural electrode grid 80 has two tails 83 of ten contacts 84 each. Contact spacings D2, D3, respectively for columns and rows of contacts 84, are typically each 10 mm, but any suitable array spacings may be used. Individual electrode discs 82 may be physically numbered for assisting the physician intraoperatively. An electrode grid may be formed in any configuration including three-dimensional. For example, a three-dimensional grid may be formed by using two or more individual electrode strips 70 or electrode grids 80, or may be a unitary structure.

FIGS. 5 and 6 respectively show dual-sided interhemispheric electrode arrays 78, 79 that are specially adapted, for example, for placement in a fissure of the brain. Such electrode placement may be utilized with the present invention. Electrode arrays 78, 79 are formed of two individual electrode arrays paired uniformly together back-to-back. Electrode arrays 78, 79, for example, may be approximately 1.0 mm thick, with electrode contacts 4.0 mm in diameter having 2.3 mm exposures. Contact spacing D4 is typically 10 mm, although any desired spacing may be used. The number of contacts may be selected according to different configurations and corresponding array formats. A marker 77 may be located on one side of the array structure, to assist in operative procedures involving, for example, locating or orienting the individually numbered electrode contacts by their respective reference to marker 77. Alternatively, a visible numbering system or any other structural keying system may be used, for example a keying indicator may be provided by rounding a portion of the electrode strip.

Figure 7:
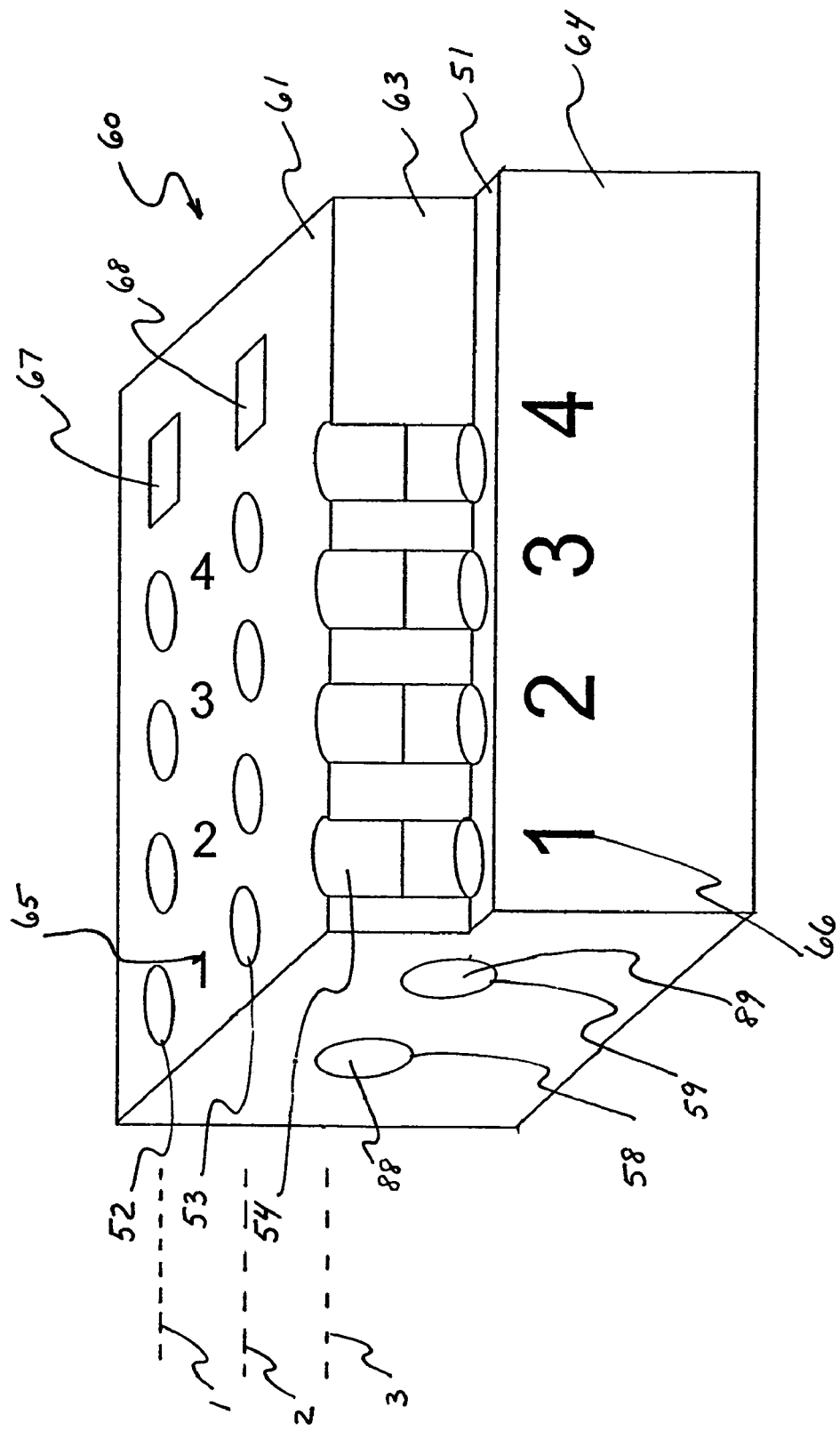
FIG. 7 is an enlarged perspective view of a connector having three rows of receptacles, according to an exemplary embodiment of the invention.

In another preferred embodiment, shown in FIG. 7, a connector 60 has a first row 1 of fully-enclosed type receptacles 52, a second row 2 of fully-enclosed type receptacles 53, and an outer row 3 of partially-exposed type receptacles 54. Connector 60 thereby accommodates a given plug having one, two, or three rows of pins. Preferably, each receptacle of a group of receptacles 52, 53, 54 are aligned with a corresponding number of a sequence of numbers 65 formed on a top surface 61 of connector 60. Keying receptacles 67, 68 are provided to assure that a plug can only be inserted in one way. As shown, keying receptacles 67, 68 are rectangular in shape, whereby keying receptacles 67, 68 are not confused with pin receptacles. The row of partially-exposed receptacles 54 are formed along a vertical surface 63 that extends from top surface 61 down to lateral surface 51. Receptacles 54 then preferably extend as fully-enclosed receptacles below surface 51. A front surface 64 has numbers 66 aligned with each pin group position and with corresponding top surface numbers 65.

In a preferred embodiment, a plug having two rows of pins is mated with connector 60 in one of two ways. First, the plug may be inserted so that the pins of the plug are inserted into rows 52, 53. Second, the plug may be inserted so that the pins of the plug are inserted into rows 53, 54. Such provides a "dual-use" connection system, discussed further below.

Each receptacle type 52, 53, 54 extends vertically as a cylinder into the body of connector 60, for each receptacle of the three rows 1, 2, 3 of receptacles. In a manner similar to that described above for connector 10, either one or two tails (not shown) may be inserted into respective tail passageways 88, 89 via respective openings 58, 59 so that ring type conductor bands of the tails are aligned with corresponding receptacle locations. Tail passageway 88 is axially centered between the first row 1 and second row 2 of receptacles. Tail passageway 89 is axially centered between the second row 2 and outer row 3 of receptacles. As a result, a tail inserted into tail passageway 88 becomes fixed in place by pins subsequently inserted into receptacles of rows 1 and 2, and a tail inserted into tail passageway 89 becomes fixed in place by pins inserted into receptacles of rows 2 and 3, in a manner as described above for connector 10 and plug 40.

For partially-exposed receptacles 19 of connector 10 and for partially-exposed receptacles 54 of connector 60, the corresponding inserted plug pins are able to be probed by direct access to the exposed pin(s). For example, an exemplary bipolar type probe 180 is shown in FIGS. 12 and 13, where a probe body 181 is lightweight and adapted for ergonomics of use by having an easily gripped non-slip surface, a probe cord 182 is secured to probe body 181 with a molded strain relief, a probe extension 183 provides a somewhat stiff yet lightweight and bendable portion that allows probe 180 to be placed in an optimized position such as by being taped temporarily in place during a surgical procedure, and where a pair of probe tips 185 are provided at a distal end of probe 180 and preferably spaced apart by a distance essentially the same as the spacing between sequential locations of connector 10. Individual probe tips 185 are exposed metal ends extending from insulation portions 184 that electrically insulate each individual conductor. In addition, shielding (not shown) may be provided in various portions of probe 180 including appropriate termination of such shielding, for example at a distal end of probe cable 182 by connection of such shielding to a body of a connector (not shown).

Probe 180 may be formed in monopolar, tripolar, and various other configurations such as a linear array. An impedance matching circuit or other components (for example a status or indicator light, a noise suppression circuit, an inline amplifier, an analog-to-digital converter, etc.) may be integrated with probe 180 such as by being part of a probe connector or by being located in probe body 181, or such may be provided as separate components, such as by being integrated in a separate adapter. In any case, probe tips 185 may be placed into contact with exposed pins (e.g., pin 42) while plug 40 is inserted into connector 10, thereby allowing, for example, continuous monitoring while providing stimulation capability. By providing direct connection of probe tips 181 with pins 42, an improved electrical connection system facilitates various surgical procedures, such as those related to cortical stimulation, without a need for disconnecting external monitoring equipment. Such a connection system facilitates monitoring of weak signals as well as stimulation using large signals. Such a connection system for electrical brain-contact devices may be electrically connected easily and quickly during surgical placement and set-up procedures.

Figure 8:
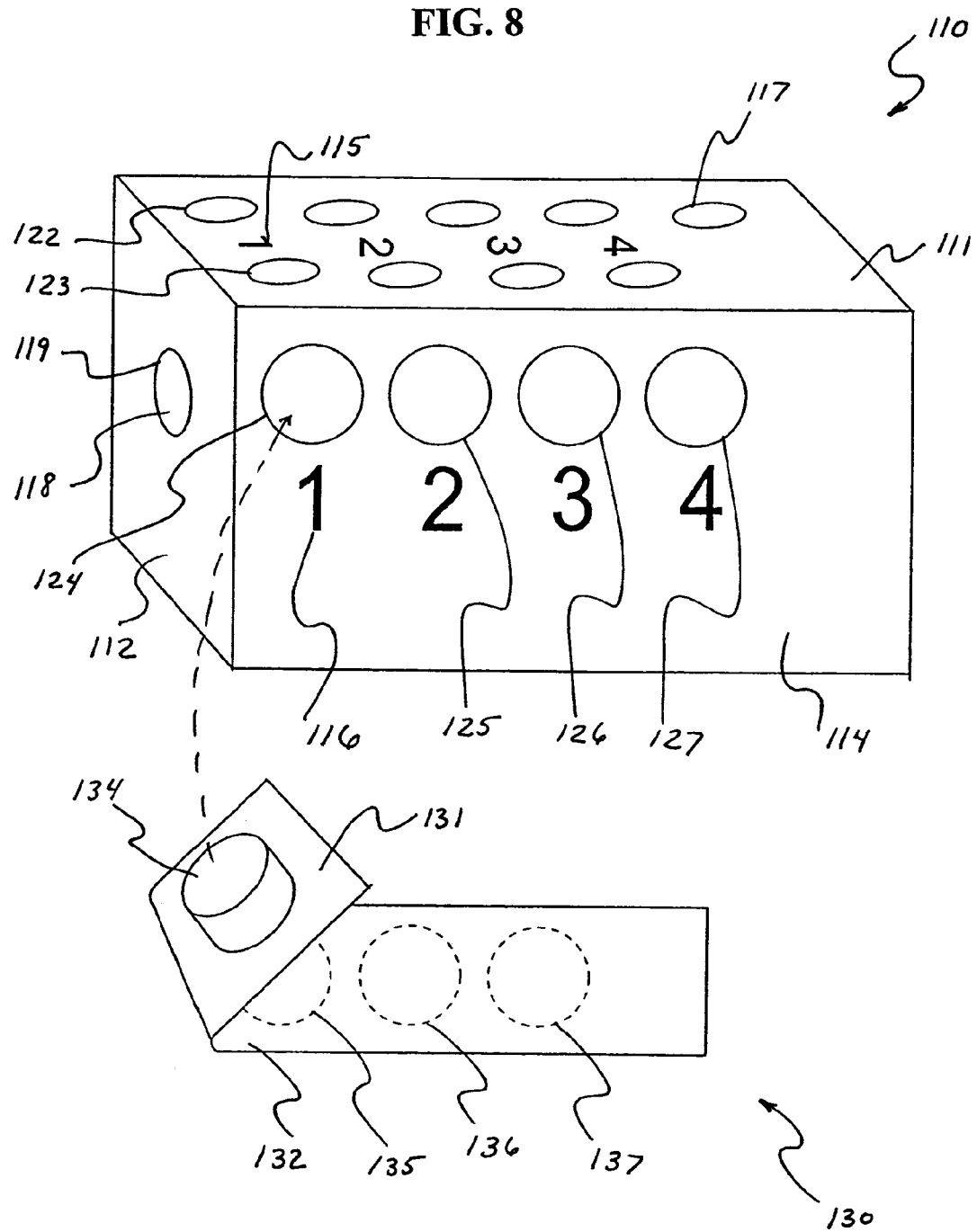
FIG. 8 is an enlarged perspective view of a connector having side access ports and a port cover strip, according to an exemplary embodiment of the invention.

FIG. 8 shows yet another exemplary embodiment of the invention, where a connector 130 includes side access holes 124–127 for receiving probe tips to be electrically mated with plug pins. As described above for other embodiments, a tail passageway 118 is axially centered between a first row of pin receptacles 122 and a second row of pin receptacles 123. In this case, both rows of pin receptacles are a fully-enclosed type. A keying receptacle 117 is located along the first row of receptacles. A series of sequential numbers 115 are formed on top surface 111, at positions corresponding to each pair of the aligned pairs of pins 122, 123. Numbers 115 are also aligned with sequential numbers 116 formed on front surface 114 at the corresponding positions of side access holes 124–127. A tail may be inserted, in a manner similar to those described above, into tail passageway 118 via an opening 119 formed in side surface 112, whereupon a plug and corresponding pins may then be inserted into receptacles 122, 123, 117 so that pairs of pins secure and are engaged with conductor rings of the tail.

Flexible strip 130 is provided for covering side access holes 124–127 when such are not being used. Flexible strip 130 is preferably formed of silicone or other resin like material and has cover strip plugs 134, 135, 136, 137 formed to project from inner surface 131 for respectively being snugly fit into side access holes 124–127. An outer surface 132 is preferably flat and may have numbers (not shown) or other markings formed thereon.

Figure 9:
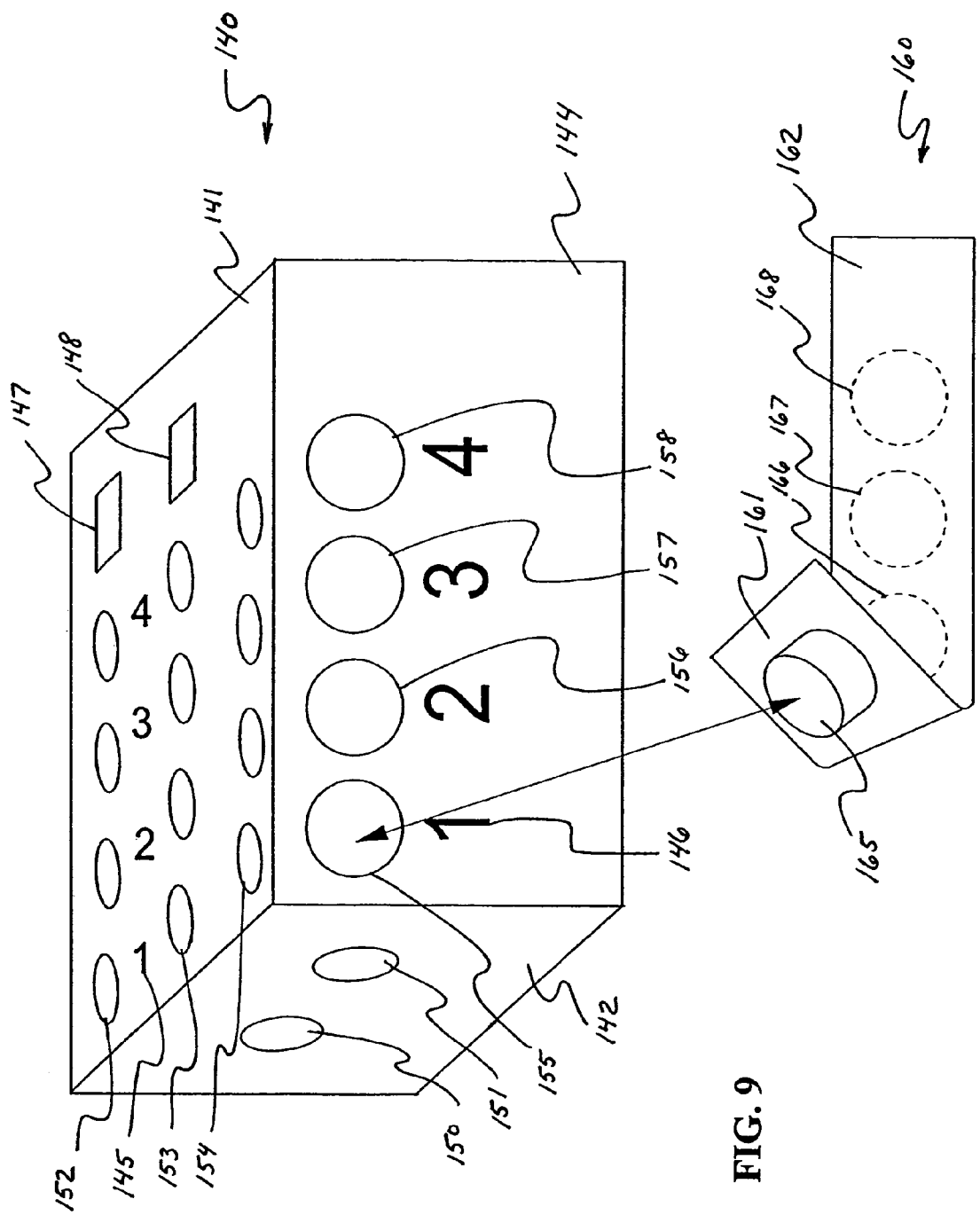
FIG. 9 is an enlarged perspective view of a three-row connector having side access ports and a port cover strip, according to an exemplary embodiment of the invention.
Figure 10:
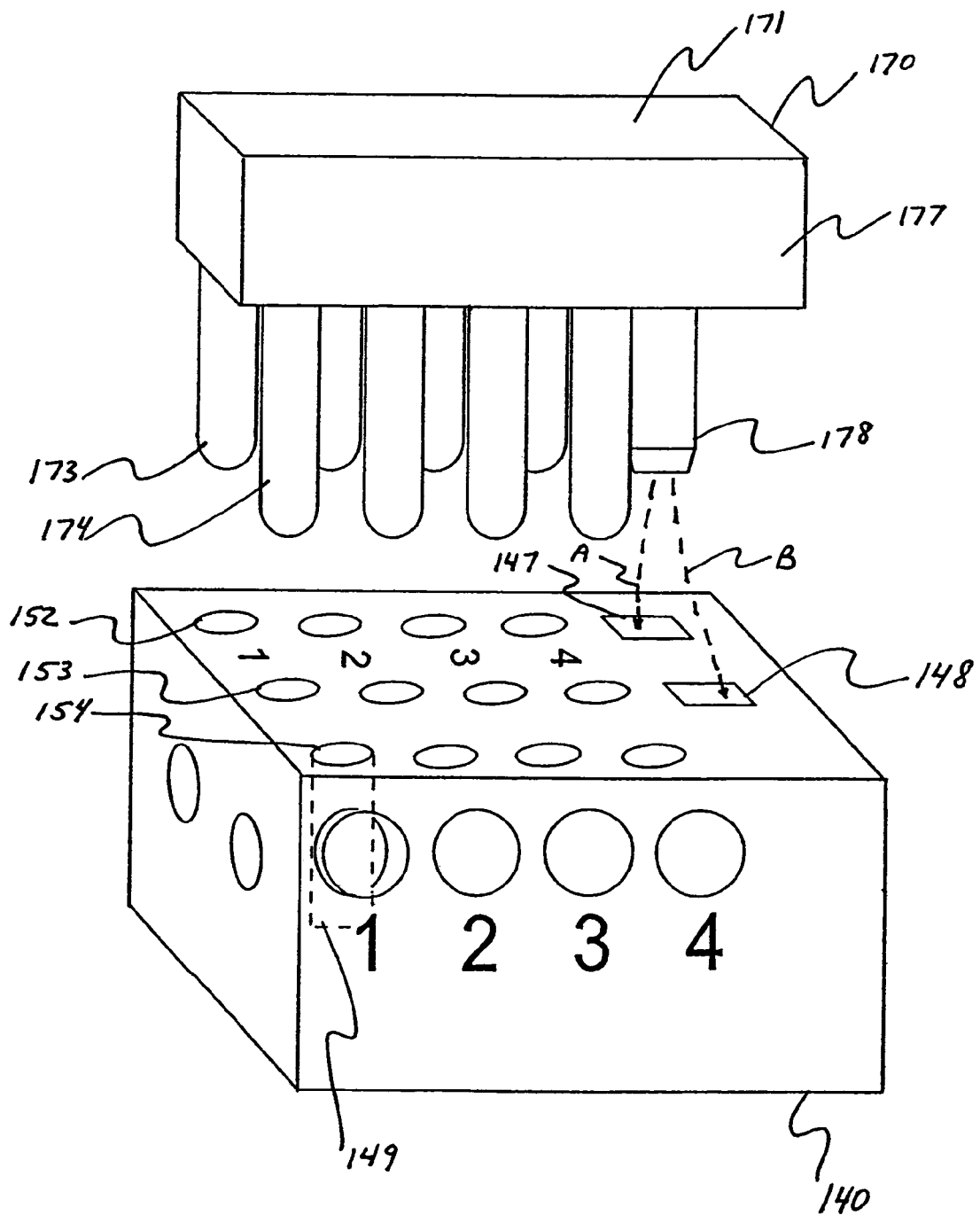
FIG. 10 is an enlarged perspective view of a connection system that includes the three-row connector of FIG. 9, according to an exemplary embodiment of the invention.

FIGS. 9 and 10 show yet another exemplary embodiment, where three rows of aligned and fully-enclosed receptacles 152, 153, 154 are provided along with corresponding side access holes 155–158 respectively aligned depthwise with each numbered receptacle position 145. Rectangular type keying receptacles 147, 148 are provided to allow a plug 170 to be inserted in either of two positions, thereby providing a dual-use connection system. For example, when keying pin 178 is inserted into keying receptacle 147 of connector 140, as denoted by the insertion labeled "A," then, as a result, a first row of pins 173 of plug 170 is inserted into rear receptacle row 152 and a second row of pins 174 is inserted into middle receptacle row 153. This "A" type insertion may be used, for example, when a stimulation probe or similar access to pins 174 is not required and it is desired to fully enclose all pins 173, 174. One type A scenario is when stimulation probe contacts are permanently installed into any of access holes 155–158 and it is desired to isolate pins 173, 174 from those stimulation probe contacts. Another type A scenario is when two separate tails have been inserted into respective ones of passageways 150, 151, and it is desired to place pins 173, 174 in contact with the tail inserted in passageway 150. Another type A scenario is when it is desired to completely prevent access to pins 174 via access holes 155–158. Another type A scenario is when it is desired to use receptacles 154 and/or access holes 155–158 for an alternate purpose such as for installation of an internal jumper (not shown), a capacitance, additional connection point(s) for monitoring, signal conditioning such as impedance matching structure, etc. Various other scenarios may be envisioned for the type A plug insertion usage.

When keying pin 178 is inserted into keying receptacle 148 of connector 140, as denoted by the insertion labeled "B," then, as a result, the first row of pins 173 of plug 170 is inserted into middle receptacle row 153 and the second row of pins 174 is inserted into front receptacle row 154. This "B" type insertion may be used, for example, when it is desired to provide stimulation probe access to pins 174 via access holes 155–158. Another type B scenario is when two tails have been inserted into respective ones of passageways 150, 151 and it is desired to connect ones of pins 173, 174 to the tail inserted in passageway 151. Various other scenarios may be envisioned for the type B plug insertion usage. By providing a connection system where a plug 170 may be inserted in one of two alternative orientations, a dual-use connection system is thereby implemented. In addition, a multiple-use connection system may be implemented to include third, fourth, and more usages, such as by providing additional rows of pin receptacles, by providing more than one keying location per receptacle row, by providing keying receptacles at opposite ends of a connector for additional insertion orientations, etc.

As shown, a first tail passageway 150 is axially centered between a rear row of receptacles 152 and a middle row of receptacles 153, so that when a tail has been inserted into tail passageway 150, pins 173, 174 respectively inserted into the rear and middle rows act to slightly compress corresponding conductive rings 32 of the tail and thereby securely hold the tail in place. In a like manner, a second tail passageway 151 is axially centered between the middle row of receptacles 153 and a front row of receptacles 154, so that when a given first or second tail has been inserted into tail passageway 151, pins 173, 174 respectively inserted into the middle and front rows act to slightly compress corresponding conductive rings 32 of the second tail and thereby securely hold the second tail in place. It is understood that a single tail may be inserted into either of passageways 150, 151 and that, alternatively, two separate tails may be individually inserted into passageways 150, 151, depending on a particular application.

Preferably, receptacles 152–154 and side access holes 155–158 are aligned with one another and with numbers 145 sequentially arranged along the rows of the top surface 141 and with the numbers 146 sequentially arranged adjacent side access holes 155–158 along the front surface 144. Numbers 145, 146 may be printed-on, painted, molded into the body of connector 140, or formed in any suitable manner.

Flexible strip 160 is provided for covering side access holes 155–158 when such are not being used. Flexible strip 160 is preferably formed of silicone or other resin like material and has cover strip plugs 165, 166, 167, 168 formed to project from inner surface 161 for respectively being snugly fit into side access holes 155–158. An outer surface 162 is preferably flat and may have numbers (not shown) or other markings formed thereon.

Plug 170 has a top surface 171 that may provide electrical access to pins 172–174 and 178, 179, such as for electrically and physically connecting a cable (not shown) to plug 170 and its pins. For example, such a cable may be a ribbon type cable secured to top surface 171 with epoxy or provided with a ribbon-to-pin adapter, etc. A front surface 177 of plug 170 may be dimensioned to be flush with front surface 144 of connector 140 when plug 170 is inserted in a type B insertion. As shown, a rear row of essentially cylindrical pins 173, and a front row of pins 174 are dimensioned to align linearly (shown depthwise) with one another and are spaced apart (axially with respect to the tail passageways) a same distance as the sequential positions of the corresponding rows of receptacles 152–154. In addition, rectangular keying pin 178 is positioned to align with corresponding receptacles 147, 148 for the A or B positions, respectively. As a result, the pins of plug 170 are dimensionally aligned with the receptacles of connector 140, so that plug 170 is easily inserted into connector 140.

When one or more tail(s) have been inserted into connector 140 and, when connector 140 is formed of a clear material and the location(s) of the inserted tail(s) is visually verified to be correct, a subsequent insertion of plug 170 acts to lock the tail(s) in place and to provide electrical connection between conductor rings 32 spaced along the given tail with corresponding pins or groups of pins of plug 170 having a same spacing. As shown, front row receptacles 154 each have a cylindrical shaft 149 that is adjacent a corresponding one of front access holes 155–158 to provide exposed access to pins 174. Front access holes 155–158 preferably are tapered or similarly dimensioned so that probe tips 185 and the like are snugly held in place while providing electrical contact between probe tip(s) 185 and corresponding ones of pins 174 of the front row of pins. Various structure may be used for assisting such electrical contact, for example by using spring-loaded contacts in probe tips 185, by maintaining an urging force of probe tip(s) 185 against a corresponding pin 174, and/or by other methods. Additional structure such as gaskets may be inserted into front access holes 155–158 and/or a clamp (not shown) may be used for securing probe 180 to connector 140 in a manner that assures stable and secure probe contact when desired. For example, a clip (not shown) may attach to a groove in the underside of connector 140 and to a groove (not shown) on top surface 171 of plug 170 or in another appropriate location. It is also understood that a quick, temporary probe contact may be desirable and, in such a case, an urging structure is unnecessary.

Although the exemplary connection systems are shown as having four lengthwise connection positions, a connector may be formed with any number of pin receptacles in a given row, with any number of receptacle rows, with adjacent receptacle rows having receptacles that are aligned depthwise in a line, that are arranged to have an offset type pattern between adjacent rows, that are arranged in a random type pattern, etc. Similarly, a given plug may be formed with various numbers of pins in configurations having rows or in other pin patterns.

In another exemplary embodiment, a system is provided that is adaptable for multi-dimensional connection between circuits, such as by providing matrix-type connectivity between different coordinate axes. For example, FIG. 14 shows a tail 190 having a bridging band 193 that, when inserted into a connector such as connector 140, acts to provide an electrical connection or short between successive positions. In one example, bridging band 193 connects a pin 174 at position "2" to a pin 174 at position "3." In this manner, pins 173 at locations "2" and "3" are also electrically shorted to the same electrical point, and circuits connected to these pins 174, 173 are thereby electrically connected at the shorting point. A given tail 190 may have single-position conductor bands 192 or bridging bands 193 in any desired combination with insulating sections 191 being used for electrically separating conductive portions therebetween.

In a further example of implementing a patchbay type of connection system, FIG. 15 shows a cross section of a multi-conductor tail 230 having a conductor band 232 that only extends around a portion of the circumference of tail 230. The remaining portion of the circumference (at a given conductor location) includes an insulating section 233. An inner portion 234 forms a core of tail 230 and may be formed of a same insulating material as insulating section 233 or of a different insulating material. A lead wire 236 is electrically connected to conductor band 232 and may itself be further insulated for at least a portion of its length as it passes through the length (not shown) of tail 230 and to eventual termination, for example, at an electrode. In order for conductor 232 to be properly aligned with a corresponding single pin of a set of pins 172, 173, 174, a key 235 is provided for insertion into a keying portion (not shown) of a given tail passageway. As a result of using a tail portion 230, individual pins may be connected to conductor 232 and corresponding lead wire 236, whereas, by comparison, at least two or three pins of a pin set are connected when, for example, a tail 30 is used.

It can be seen that the bridging conductive band 193 of FIG. 14 provides a matrix or patchbay type of connection option in the so-called "X-axis," and the partial conductive ring 232 of FIG. 15 provides a patchbay connection option in the "Z-axis." A "Y-axis" patchbay option may also be implemented, such as by using tail passageways that are aligned vertically while also being centered between pins of a sequential pin location. In such a case, an upper tail may have a circular conductive band 32, a partial conductive band 232, a bridging band 193, or an insulating spacer 191 at a given location, while a lower tail may have a different one of these optional tail members at its location with a same "X" coordinate and a different "Y" coordinate. By mixing and matching the three-dimensional connection options, a desired interconnectivity may be easily implemented. For example, a color-coded, numbered, and or kitted set of connection components may be bagged together for a particular surgical procedure and corresponding equipment setup. Such predetermined interconnectivity helps eliminate a use of adapters and the like, and resultant likelihood of error, equipment breakage, etc.

FIG. 16 shows yet another exemplary embodiment, where the connector 140 of FIG. 9 is used with a three-row plug 270 to assure that plug 270 can only be inserted in a single correct orientation and for providing additional connection possibilities. In addition, the dual tail passageways 150, 151 may be used for receiving two separate tails. Since first tail passageway 150 is axially centered between rear row of receptacles 152 and middle row of receptacles 153, when a tail has been inserted into first tail passageway 150, pins 272, 273 respectively inserted into the rear and middle rows act to slightly compress corresponding conductive rings 32 of the tail and thereby securely hold the tail in place. In a like manner, since second tail passageway 151 is axially centered between middle row of receptacles 153 and front row of receptacles 154, when a second tail has been inserted into tail passageway 151, pins 273, 274 respectively inserted into the middle and front rows act to slightly compress corresponding conductive rings 32 of the second tail and thereby securely hold the second tail in place.

Plug 270 has a top surface 271 that may provide electrical access to pins 272–274 and 198, such as for electrically and physically connecting a cable (not shown) to plug 270 and its pins, in a manner similar to that used for connecting a cable to plug 170, described above. A front surface 277 of plug 270 may be dimensioned to be flush with front surface 144 of connector 140 when plug 270 is inserted. As shown, a rear row of essentially cylindrical pins 272, a middle row of pins 273, and a front row of pins 274 are dimensioned to align linearly (shown depthwise) with one another and are spaced apart (axially with respect to the tail passageways) a same distance as the sequential positions of the corresponding rows of receptacles 152–154. In addition, rectangular keying pin 198 is positioned to align with corresponding receptacle 148. As a result, the pins of plug 270 are dimensionally aligned with the receptacles of connector 140, so that plug 270 is easily inserted into connector 140.

When one or more tail(s) have been inserted into connector 140 and, when connector 140 is formed of a clear material and the location(s) of the inserted tail(s) is verified to be correct, a subsequent insertion of plug 270 acts to lock the tail(s) in place and to provide electrical connection between conductor rings 32 spaced along the given tail with corresponding pins or groups of pins of plug 270 having a same spacing. As shown, front row receptacles 154 each have a cylindrical shaft 149 that is adjacent a corresponding one of front access holes 155–158 to provide exposed access to pins 274.

Plug 270, when used with customized structures such as patchbay type tail 190, keyed tail 230, and others, allows a user to access, for example, certain ones of pins 272, 273, 274 in combination with others of the pins and/or conductive tail bands, thereby providing adaptable structure for implementing any desired connection patch. For example, by removing selected ones of pins 272, 273, 274, by connecting a portion of a conductive tail band to only a single pin, by using a bridging type conductive band 193, and by any other connection scheme and associated structure, a three-dimensional customized patch may be effected for connecting any chosen points of a three-dimensional array.

FIG. 17 shows an alternative embodiment of a connector 260 having a keying receptacle hole 261 at a same end of connector 260 as a passageway entry hole 263. Pin receptacle holes 265 are on the distal side of keying receptacle with respect to keying adapter 261. Connector 260 is adapted for inserting a tail 30 into a passageway 264 via passageway entry hole 263 and then pushed all the way to endstop 262. As a result of implementing a connection system using connector 260, any of several additional scenarios may be accommodated. For example, a cable (not shown) may be attached to plug 40 to feed plug 40 from a direction that passes keying pin 47. In such a case, it may be desirable to bundle or tie-together the cable with a tail 30 to be inserted into connector 260. In such a case, a wire tie may be used to harness tail 30 together with the cable so that the harness only approaches connector 260 from a single direction. In another scenario, the pins from a given plug 40 may be patched to a different set of circuits by simply exchanging connector 260 for a connector 10 (e.g., FIG. 2), whereby the conductive bands 32 of tail 30 are connected to different ones of the pins of plug 40 as a result of the reversal in orientation between plug 40 and tail 30 effected by the exchange of connectors.

As a result of implementing some of the disclosed embodiments, an electrical connector is provided that resists breakage of lead wires during insertion of brain-contact devices, that may be implemented to provide rapid and accurate electrical hookup of large numbers of electrodes and lead wires during surgical procedures, and that allows electrical connection of plural lead wires in a manner which is simple in construction and operation.

In various other options, a given connector may be implemented as a unitary device or as a plurality of sub-blocks as components of the whole. It may be advantageous to implement such a segmented system, for example, when it is desired to change connectivity for selected patches, to feed additional circuits, etc., and for allowing a connector to be sized to accommodate any number of lead-wire terminals and individual conductors. Finger-grip protrusions (not shown) may be included to facilitate detachment of a connector from the conductors and/or plugs used therewith, and also aid in detachment of one sub-block from another.

While the principles of the invention have been shown and described in connection with specific embodiments, it is to be understood that such embodiments are by way of example and are not limiting. Consequently, variations and modifications commensurate with the above teachings, and with the skill and knowledge of the relevant art, are within the scope of the present invention. The embodiments described herein are intended to illustrate best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A multiple-use connection system, comprising:
an elongate body, having a lengthwise top surface, having first and second lengthwise side surfaces respectively adjoining opposite lengthwise sides of the lengthwise top surface, and having a first lengthwise tail-receiving passage for receiving a tail having a plurality of annular conductors axially-spaced along a circumference of the tail; and
first and second rows of axially-spaced pin receptacle spaces extending from the lengthwise top surface into the elongate body, each pin receptacle space having a longitudinal axis orthogonal to the longitudinal axis of the first lengthwise tail-receiving passage, each pin receptacle space intersecting the first lengthwise tail-receiving passage; and
a plurality of individual access holes formed in the first lengthwise side surface and laterally connecting respective ones of the first row of pin receptacle spaces with a space external to the elongate body.

2. The multiple-use connection system of claim 1, wherein respective adjacent spaces of the first and second rows of axially-spaced pin receptacle spaces are laterally aligned with one another as individual pin receptacle space pairs.

3. The multiple-use connection system of claim 1, wherein the first axial tail-receiving passage is centered between the first and second rows of pin receptacle spaces.

4. The multiple-use connection system of claim 1, further comprising:
the tail, the axial spacing of the plurality of annular conductors being in registration with axial spacing of the first and second rows of axially-spaced pin receptacle spaces when the tail is inserted into the first lengthwise tail-receiving passage; and
a plug having at least two rows of pins axially spaced in correspondence with the plurality of annular conductors,
wherein, when the tail and plug are both inserted/plugged into the elongate body, laterally-adjacent pins positioned in respective ones of the first and second rows of axially-spaced pin receptacle spaces form pin pairs in contact with respective ones of the annular contacts at opposite sides thereof.

5. The multiple-use connection system of claim 4, wherein the elongate body further includes an unpaired pin receptacle space aligned with one of the rows of axially-spaced pin receptacle spaces, wherein the plug includes an unpaired pin so that the unpaired pin and unpaired pin receptacle space effect keying of the plug and elongate housing to one another.

6. The multiple-use connection system of claim 1, wherein the elongate body comprises at least three essentially parallel rows of axially-spaced pin receptacle spaces.

7. The multiple-use connection system of claim 6, wherein the elongate body further comprises a second axial tail-receiving passage, the first and second axial tail-receiving passages respectively being centered between adjacent ones of the parallel rows of axially-spaced pin receptacle spaces.

8. The multiple-use connection system of claim 1, further comprising a plurality of plugs dimensioned for covering the plurality of individual access holes when not in use.

9. The multiple-use connection system of claim 8, wherein the plurality of plugs are attached to one another as a strip of plugs.

10. The multiple-use connection system of claim 1, further comprising a plug having two rows of pins in registration with spaces of the first and second rows of axially-spaced pin receptacle spaces, so that the pins extend into respective ones of the spaces to intersect the first lengthwise tail-receiving passage when the plug is plugged into the elongate body.

11. The multiple-use connection system of claim 10, further comprising the tail, wherein when the tail is first inserted into the first lengthwise tail-receiving passage, a subsequent plugging-in of the plug into the elongate body causes at least some of the pins of the plug to snugly engage respective ones of the annular conductors.

12. The multiple-use connection system of claim 11, wherein the system is structured so that the plugging-in of the plug into the elongate body effects a locking in place of the tail.

13. The multiple-use connection system of claim 11, further comprising a multiconductor cable terminating at its first end by connection of individual conductors to the pins of the plug, and having a second end.

14. The multiple-use connection system of claim 13, wherein the multiconductor cable terminates at its second end as a plurality of individual connectors corresponding to the individual conductors.

15. The multiple-use connection system of claim 13, further comprising an electromagnetic interference (EMI)-resistant hood for electrically shielding the connection system, wherein the multiconductor cable is electrically shielded and the EMI-resistant hood is formed of a non-magnetic shielding material.

16. A multiple-use connection system, comprising:
an elongate body having first and second lengthwise top surfaces stepped with respect to one another, having a first lengthwise side surface adjoining one lengthwise side of the first lengthwise top surface, having a second lengthwise side surface effecting a step by adjoining both the other lengthwise side of the first lengthwise top surface and a one lengthwise side of the second lengthwise top surface, having a third lengthwise side surface adjoining the other lengthwise side surface of the second lengthwise top surface, and having a first lengthwise tail-receiving passage adapted for receiving a tail having a plurality of annular conductors axially-spaced along a circumference of the tail;
first and second rows of axially-spaced pin receptacle spaces formed in the elongate body, each pin receptacle space having a longitudinal axis orthogonal to respective planes of the top surfaces, each pin receptacle space intersecting the tail-receiving passage, each pin receptacle space of the first row of pin receptacle spaces being divided by the second lengthwise side surface into a lateral portion bounded by the elongate body and an exposed lateral portion.

17. The multiple-use connection system of claim 16, wherein respective adjacent spaces of the first and second rows of axially-spaced pin receptacle spaces are laterally aligned with one another as individual pin receptacle space pairs.

18. The multiple-use connection system of claim 16, wherein the first axial tail-receiving passage is centered between the first and second rows of pin receptacle spaces.

19. The multiple-use connection system of claim 16, further comprising a hinged cover for covering and uncovering the exposed lateral portions of the first row of pin receptacle spaces.

20. The multiple-use connection system of claim 16, further comprising:
the tail, the axial spacing of the plurality of annular conductors being in registration with axial spacing of the first and second rows of axially-spaced pin receptacle spaces when the tail is inserted into the first lengthwise tail-receiving passage; and
a plug having at least two rows of pins axially spaced in correspondence with the plurality of annular conductors,
wherein, when the tail and plug are both inserted/plugged into the elongate body, laterally-adjacent pins positioned in respective ones of the first and second rows of axially-spaced pin receptacle spaces form pin pairs in contact with respective ones of the annular contacts at opposite sides thereof.

21. The multiple-use connection system of claim 20, wherein the elongate body further includes an unpaired pin receptacle space aligned with one of the rows of axially-spaced pin receptacle spaces, wherein the plug includes an unpaired pin so that the unpaired pin and unpaired pin receptacle space effect keying of the plug and elongate housing to one another.

22. The multiple-use connection system of claim 16, wherein the elongate body comprises at least three essentially parallel rows of axially-spaced pin receptacle spaces.

23. The multiple-use connection system of claim 22, wherein the elongate body further comprises a second axial tail-receiving passage, the first and second axial tail-receiving passages respectively being centered between adjacent ones of the parallel rows of axially-spaced pin receptacle spaces.

24. The multiple-use connection system of claim 16, further comprising a plug having two rows of pins in registration with spaces of the first and second rows of axially-spaced pin receptacle spaces, so that the pins extend into respective ones of the spaces to intersect the first lengthwise tail-receiving passage when the plug is plugged into the elongate body.

25. The multiple-use connection system of claim 24, further comprising the tail, wherein when the tail is first inserted into the first lengthwise tail-receiving passage, a subsequent plugging-in of the plug into the elongate body causes at least some of the pins of the plug to snugly engage respective ones of the annular conductors.

26. The multiple-use connection system of claim 25, wherein the system is structured so that the plugging-in of the plug into the elongate body effects a locking in place of the tail.

27. The multiple-use connection system of claim 25, further comprising a multiconductor cable terminating at its first end by connection of individual conductors to the pins of the plug, and having a second end.

28. The multiple-use connection system of claim 27, wherein the multiconductor cable terminates at its second end as a plurality of individual connectors corresponding to the individual conductors.

29. The multiple-use connection system of claim 27, further comprising an electromagnetic interference (EMI)-resistant hood for electrically shielding the connection system, wherein the multiconductor cable is electrically shielded and the EMI-resistant hood is formed of a non-magnetic shielding material.

30. A patchbay for selectively connecting pairs of connector pins with ones of a plurality of tail conductors comprising:
an insulating body having two lengthwise side surfaces, having an axial passageway adapted for receiving a tail with the plurality of tail conductors, and having pairs of aligned pin receptacle spaces, the pairs of pin receptacle spaces being axially spaced from one another, one pin receptacle of each of the pairs of pin receptacle spaces having a pin receptacle space exposed along the pin axis and a pin receptacle space fully enclosed by the insulating body, the exposed pin receptacle spaces being adapted for being directly probed along one of the lengthwise side surfaces of the insulating body;
the tail; and
a plug having at least two rows of conductive pins axially spaced in correspondence with the plurality of conductors of the tail,
wherein ones of the plurality of tail conductors are selectively connectable to ones of the conductive pins of the plug by at least one of a first and second structure, the first structure including interconnection, within the tail, and the second structure including probe being physically connected to the conductive pins.

31. The patchbay of claim 30, wherein the first structure includes annular segmentation of at least one of the plurality of tail conductors into a conductive portion and an insulated portion, wherein the conductive portion connects at least two longitudinally-adjacent ones of the conductive pins when the tail and plug are installed in the insulating body.

32. The patchbay of claim 30, wherein axial spacing of the plurality of tail conductors is in registration with axial spacing of the pairs of aligned pin receptacle spaces when the tail is inserted into the axial passageway.

* * * * *

UNITED STATES PATENT AND TRADEMARK OFFICE
CERTIFICATE OF CORRECTION

| | | |
|---|---|---|
| PATENT NO. | : 7,134,919 B2 | Page 1 of 1 |
| APPLICATION NO. | : 11/029269 | |
| DATED | : November 14, 2006 | |
| INVENTOR(S) | : David A. Putz | |

It is certified that error appears in the above-identified patent and that said Letters Patent is hereby corrected as shown below:

Column 18, line 36, after "including" insert --direct--.

Signed and Sealed this

Twenty-fourth Day of April, 2007

JON W. DUDAS
*Director of the United States Patent and Trademark Office*